United States Patent
Fernandes de Oliveira et al.

(10) Patent No.: US 9,492,372 B2
(45) Date of Patent: Nov. 15, 2016

(54) **PROCESS FOR PREPARING *SAPUCAINHA* OIL OR BUTTER, COSMETIC OR PHARMACEUTICAL COMPOSITION AND USE OF THE *SAPUCAINHA* OIL OR BUTTER**

(75) Inventors: Amanda Fernandes de Oliveira, Campinas SP (BR); Roberta Roesler, Campinas SP (BR); José Renato Cagnon, Belém PA (BR); Débora Cristina Castellani, Jundiai SP (BR)

(73) Assignee: Natura Cosmeticos S.A., Itapecerica da Serra—SP (BR)

( * ) Notice: Subject to any disclaimer, the term of this patent is extended or adjusted under 35 U.S.C. 154(b) by 1025 days.

(21) Appl. No.: 12/666,397

(22) PCT Filed: Jun. 10, 2008

(86) PCT No.: PCT/BR2008/000166
§ 371 (c)(1),
(2), (4) Date: Sep. 28, 2010

(87) PCT Pub. No.: WO2009/000055
PCT Pub. Date: Dec. 31, 2008

(65) Prior Publication Data
US 2011/0038970 A1   Feb. 17, 2011

(30) Foreign Application Priority Data
Jun. 27, 2007  (FR) ..................... 07 04621

(51) Int. Cl.
| *A61K 36/185* | (2006.01) |
| *A61K 8/92* | (2006.01) |
| *C11B 1/06* | (2006.01) |
| *C11B 3/00* | (2006.01) |
| *C11B 3/04* | (2006.01) |
| *C11B 3/14* | (2006.01) |

(52) U.S. Cl.
CPC ............. *A61K 8/922* (2013.01); *A61K 36/185* (2013.01); *C11B 1/06* (2013.01); *C11B 3/008* (2013.01); *C11B 3/04* (2013.01); *C11B 3/14* (2013.01)

(58) Field of Classification Search
CPC .................................................... A61K 36/185
USPC .......................................................... 424/776
See application file for complete search history.

(56) References Cited

U.S. PATENT DOCUMENTS

| 1,580,664 | A | * | 4/1926 | Graif, Jr. ...................... 24/601.1 |
| 4,152,416 | A | | 5/1979 | Spitzer et al. |
| 4,588,745 | A | | 5/1986 | Bessler |
| 5,342,965 | A | | 8/1994 | Behr et al. |
| 5,514,712 | A | * | 5/1996 | LeClere ........................ 514/530 |
| 5,683,683 | A | | 11/1997 | Scafidi |

FOREIGN PATENT DOCUMENTS

| FR | 2 518 402 | | 6/1983 |
| FR | 2518402 | A * | 6/1983 |
| FR | 2 876 908 | | 4/2006 |
| FR | 2 876 909 A1 | | 4/2006 |
| GB | 369 062 A | | 3/1932 |
| GB | 1 580 664 | | 12/1980 |

OTHER PUBLICATIONS

Database Caplus; Chemical Abstracts Service, Columbus, Ohio, XP002472586.
Search Report and Written Opinion for PCT/BR2008/000166 dated Sep. 10, 2008.
Lima, J.A., et al.; "Anti-Inflammatory and Antinociceptive Activities of an Acid Fraction of the Seeds of Carpotroche Brasiliensis"; *Brazilian Journal of Medical and Biological Research* (2005) 38: 1095-1103.
International Preliminary Report on Patentability from International Application No. PCT/BR2008/000166, dated Aug. 19, 2009.

* cited by examiner

*Primary Examiner* — Chris R Tate
*Assistant Examiner* — Deborah Davis
(74) *Attorney, Agent, or Firm* — Alston & Bird LLP

(57) ABSTRACT

The present invention relates to a process for preparing a *sapucainha* oil butter which enables obtaining an improved product for use in cosmetic compositions instead of silicone and fatty esters compounds.

9 Claims, No Drawings

PROCESS FOR PREPARING *SAPUCAINHA* OIL OR BUTTER, COSMETIC OR PHARMACEUTICAL COMPOSITION AND USE OF THE *SAPUCAINHA* OIL OR BUTTER

FIELD OF THE INVENTION

The present invention relates to a process for preparing a stabilized oil or butter and to cosmetic and pharmaceutical compositions containing the *sapucainha* oil or butter thus obtained.

BACKGROUND OF THE INVENTION

The *sapucainha* oil whose INCI registration as "name: Carpotroche brasiliensis (*sapucainha*) butter seed" is still pending, has similarities in its fatty composition with the oil described in the literature called chaulmoogra oil. The chaulmoogra oil has been known and used for centuries with therapeutic purposes and several documents in the literature describe its specific application for treating leprosy, its anti-inflammatory activity and its use in cosmetic compositions.

The chaulmoogra oil may be extracted, among other species, from plants of species popularly known in Brazil by the names *sapucainha*, papo-de-anjo, pau-de-cachimbo, pau-de-lepra, and others. The oil is normally extracted from the *sapucainha* seeds and its topical cosmetic use has been studied for application in several skin affections. Its therapeutic application is also known, and the chaulmoogra oil, because of its differentiated fatty composition, was largely used against leprosy. There are also reports of its anti-inflammatory activity.

Document U.S. Pat. No. 5,514,712 discloses the use of chaulmoogra oils in cosmetic and pharmaceutical compositions for harmonizing the pigmentation of the skin. The oils may be in the form of salt or ester. One of the major sources of this oil is the *Carpotroche brasiliensis* (*sapucainha*) plant.

Document FR 2 876 908 discloses the use of the chaulmoogra oil and/or components thereof in cosmetic and/or pharmaceutical compositions for treating or preventing the excess of fat and cellulitis. One of the major sources of this oil is the *Carpotroche brasiliensis* (*sapucainha*) plant.

Document FR 2 876 909, in turn, discloses a cosmetic and/or pharmaceutical composition to prevent or treat the excess of cellulitis and fat comprising the combination of one or more xanthinic bases and chaulmoogra oil and/or its components.

Another prior-art document disclosing the use of chaulmoogra oil in cosmetology is document FR 2 518 402, which mentions preferable applications in skin treatments such as acne, and hair care and makeup compositions. One of the major sources of this oil is the *Carpotroche brasiliensis* (*sapucainha*) plant.

Document GB 369 062 discloses compositions of antileprotic medicaments. In accordance with this document, the fatty acids, specially the chaulmoogric and hydnocarpic acids, obtained by saponification of the oils of flacourtiaceous seeds are purified by crystallization from alcohol and esterified with aliphatic, hydroaromatic or aromaticaliphatic alcohols to form the corresponding esters. Reduction of these esters gives the corresponding mixed alcohols, which may then be treated with acylating agents to produce their acyl esters. Plants of the Flacourtiaceae family mentioned are *Taraktogenos kurzii, Hydnocarpus wightiana, Hydnocarpus anthelmintica, Carpotroche brasiliensis* and *Caloncoba echinata*. The products are therapeutically useful.

Document U.S. Pat. No. 5,683,683 discloses a body wash composition comprising an anionic cleansing surfactant, such as an alkyl ether sulfate or an alkyl sulfate, a polymeric cationic conditioning compound, and a quaternized phosphate ester. This composition may also contain an oil, such as the chaulmoogra oil.

Document U.S. Pat. No. 5,342,965 discloses a process for producing branched fatty substances with the addition of maleic anhydride onto unsaturated fatty acids or lower alkyl esters thereof. The use of the chaulmoogric acid as raw material is foreseen.

U.S. Pat. No. 4,152,416 discloses aerosol antiperspirant compositions, capable of dispensing astringent salt with low mistiness and dustiness. The addition of cycloaliphatic acids as chaulmoogra oil fatty acids is provided.

The 2005 scientific paper "Anti-inflammatory and antinociceptive activities of an acid fraction of the seeds of *Carpotroche brasiliensis* (Raddi)" by Lima, -J-A; Oliveira, -A-S; de-Miranda, -A-L-P; Rezende, -C-M; Pinto, -A-C discloses the intrinsic activities of *sapucainha*, describing, in particular, its anti-inflammatory activity.

However, all the cosmetic and/or pharmaceutical compositions and uses described and provided for *sapucainha* oils also comprise the addition of silicones and fatty esters. On the other hand, there is a growing interest of the cosmetic and pharmaceutical industry in obtaining products free from chemically-produced silicones and fatty esters, which cause environmental impact.

SUMMARY OF THE INVENTION

The present invention relates to a process for preparing a *sapucainha* oil or butter comprising the steps of:
a) providing seeds from *sapucainha* plant species;
b) drying and pressing said seeds for extracting the oil;
b) filtering the oil obtained in step (b);
d) treating the filtrate resulting from step (c) with an organic acid and a acid-activated clay;
e) keeping the product obtained in (d) under vacuum for a suitable time period enabling the adsorption of the undesirable compounds.
f) filtering the material resulting from step (e) and submitting the filtrate to vapor distillation;
g) adding to the distillate a sequestering agent and a antioxidant agent for obtaining the final *sapucainha* oil or butter product.

The present invention further relates to a cosmetic or pharmaceutical composition comprising *sapucainha* oil or butter, cosmetically or pharmaceutically acceptable salts or esters thereof, and which is free from silicone and other fatty esters.

The present invention further relates to a cosmetic or pharmaceutical composition comprising *sapucainha* oil or butter, cosmetically or pharmaceutically acceptable salts or esters thereof, which is free from silicone and other fatty esters.

DETAILED DESCRIPTION OF THE INVENTION

The present invention relates to a process for preparing the *sapucainha* oil or butter. The only difference between the oil and the butter lies in the temperature in which the oil is submitted (PF approx. 32° C.). Because of the fatty composition, oils are liquid at ambient temperature and butters are solid. In the case of *sapucainha*, for example, because of its fatty composition, the most correct term to define the material used is *sapucainha* "butter". However, chaulmoogra oils and butters may be used to achieve the objects of the present invention.

As examples of plant species (*sapucainha*) which may be used as a source of oils and butters useful in the present invention, the following may be cited:
*Taraktogenos kurzii*
*Hydnocarpus wightiana*
*Hydnocarpus heterophylla*
*Hydnocarpus anthelmintica*
*Hydnocarpus alpina*
*Hydnocarpus caulifora*
*Hydnocarpus dawnensis*
*Hydnocarpus hutchinsonni*
*Hydnocarpus ovoidea*
*Hydnocarpus subfalcata*
*Hydnocarpus venenata*
*Hydnocarpus verrucosa*
*Hydnocarpus woodii*
*Oconba echinata*, whose butter is called "Gorli butter"
*Caloncoba welwitschii*
*Carpotroche amazonensis*
*Carpotroche bahiensis*
*Carpotroche brasiliensis*
*Carpotroche brasiliensis* var. *bahiensis*
*Carpotroche brasiliensis* var. *longifolia*
*Asteriastigma macrocarpa*
*Mayna brasiliensis*
*Mayna odorata*
*Lindakeria dentata*
*Caloncoba glauca*

According to a preferred embodiment of the invention, the *sapucainha* oil or butter is obtained from the *Carpotroche brasiliensis/carpotroche amazonensis* species.

The *sapucainha* butter is obtained by an extraction and stabilization method that enables the resulting oil or butter to be advantageously used in cosmetic or pharmaceutical compositions instead of silicones and fatty esters.

The process for preparing the *sapucainha* oil or butter according to the present invention comprises the steps of:
a) providing seeds from the *sapucainha* plant species;
b) drying and pressing said seeds for extracting the oil;
c) filtering the oil obtained in step (b);
d) treating the filtrate resulting from step (c) with an organic acid and a acid-activated clay;
e) keeping the product obtained in (d) under vacuum for a suitable period of time, until the material becomes clear, enabling the adsorption of the undesirable compounds;
f) filtering the material resulting from step (e) and submitting the filtrate to vapor distillation;
g) adding to the distillate a sequestering agent and a antioxidant agent for obtaining the final *sapucainha* oil or butter product.

The process of extracting the *sapucainha* oil or butter useful for the present invention comprises, in the first place, a selection of fruits using those with a suitable ripening grade. The skin and pulp of fruits are removed manually or by means of a depulper, and the seeds are dried so that the extraction process proper may start. Drying may be performed in open air or in a greenhouse with forced air circulation.

In order to extract the butter, a mechanical press is preferably used. The seeds are added and pressed by physical pressing. After that, the butter obtained is filtered for the removal of impurities/residues through a press filter. The yield of extraction after filtration is generally around 25-30%. The main parameters to be controlled during the process are: moisture, acidity value, peroxide value, unsaponifiable matter, saponification value and iodine value.

According to a preferred embodiment of the present invention, the process for obtaining the *sapucainha* butter comprises the following steps:
selecting the fruits pursuant to their ripening stage, separating those with a suitable ripening grade;
separating seeds from the pulp and the skin of the fruit;
drying the seeds;
physical pressing of the seeds;
filtering the butter with the addition of a filtering agent (silicon oxide, aluminium oxide, ferric oxide, calcium oxide, magnesium oxide, sodium oxide, potassium oxide, among others);
treating the butter with an organic acid (citric acid, phosphoric acid, oxalic acid, among others) and acid-activated clay during a certain period of time (15-60 min) under rigorous stirring;
clarifying the butter for a certain period of time (15-60 min) under vacuum at a certain temperature (0-100° C.);
filtering under vacuum;
vapor distilling the undesirable compounds at a certain temperature (160°-240° C.) during a certain period of time (1-2 h) under vacuum;
adding a certain amount of sequestering agent and a certain amount of antioxidant (0.1-1% sequestering; citric acid, phosphoric acid, oxalic acid, among others, and 0.01-0.1% antioxidant: Butylhydroxyanisole (BHA), ter-butyl hydroquinone (TBHQ), butylated hydroxytoluene (BHT), among others)

The process described above enables the extraction and also the stabilization of the oil or butter obtained and aims at removing specially metal ions such as iron (substances found in high frequency and in high amounts in oleaginous seeds of the Amazon and Rainforest biomes) and other compounds and/or undesirable characteristics (odor, free fatty acids, phospholipids, oxidation compounds such as peroxides, aldehydes, etc) which cause butter degradation and specially degradation of the final compositions to which it is applied. It should be noted that the odor of the raw non-stabilized butter cannot be masked by other fragrances making is application virtually unfeasible in cosmetic formulations. In addition, high amounts of metals cause accelerated oxidation of the butter and the cosmetic formulas to which it was added, causing an unpleasant odor, darkening as well as the production of free radicals, which are mainly related to skin ageing. Some characteristics differentiating a raw *sapucainha* butter and the stabilized butter obtained according to the present invention are shown in Table 1:

TABLE 1

Comparative data between the raw sapucainha butter and the stabilized butter obtained according to the process of the present invention.

| | | Raw Sapucainha Butter | Stabilized Sapucainha Butter |
|---|---|---|---|
| Metals (ppm) | Iron (ppm) | 39.1 | 8.8 |
| | Copper (ppm) | <0.1 | 8.8 |
| | Phosphorous (ppm) | 144.2 | 75.7 |
| Stability | Oxidation induction time (h)-Rancimat | 12 | >40 |

TABLE 1-continued

Comparative data between the raw sapucainha
butter and the stabilized butter obtained
according to the process of the present invention.

|  | Raw Sapucainha Butter | Stabilized Sapucainha Butter |
|---|---|---|
| Shelf-life estimate (months) | 6 | >20 |
| Odor | strong (characteristic) | inodorous |

The *sapucainha* butter obtained according to the process described above, further to being improved for use in cosmetic and pharmaceutical compositions, goes through a process containing purely physical steps, which may be considered "green technology", that is to say, the process of the invention is contributing to environmental protection and does not generate byproducts or residues in the *sapucainha* butter, as do chemical processes, such as, for example, extraction by solvents, neutralization with strong bases, etc. This aspect is extremely relevant, because currently there is a growing interest in vegetable raw materials obtained exclusively by physical processes which may replace cosmetic raw materials such as silicones that are manufactured from nonrenewable resources and by chemical processes.

The present invention also relates to cosmetic and pharmaceutical compositions containing *sapucainha* oil obtained with a process such as defined above, and cosmetically or pharmaceutically acceptable salts or esters thereof.

The *sapucainha* oil or butter, is preferably present in the cosmetic or pharmaceutical compositions in a range of from 1 to 10%, by weight, more preferably from 3 to 10%, by weight, even more preferably from 5 to 10%, by weight, based on the total weight of the final composition.

The cosmetic and pharmaceutical compositions of the present invention may further contain other usual ingredients of this type of formulation, such as emollients, surfactants, antioxidants, cosmetically or pharmaceutically acceptable carriers, etc.

The present invention will be illustrated by the examples below:

EXAMPLES

Example 1

Preparation of *Sapucainha* Butter According to the Present Invention

Fruits were selected according to their ripening stage, and those considered to be ripe were used. The seeds were separated from the fruit's pulp, and this separation was made manually and by means of a depulper.

The seeds were dried by means of solar exposure, and the final moisture content was controlled to remain between 7 and 9% so that they can be stored without the risk of contamination and degradation. The dry seeds were pressed and the butter was filtered with the addition of a filtering agent (filtering agent rich in silicon oxide, aluminium oxide, sodium oxide and potassium oxide).

Approximately 500 g of *sapucainha* oil as obtained above were put in a beaker and heated at 90° C. for 5 min. 2.5 g of a citric acid solution 30% were added. The solution was stirred for 10 min.

The mixture oil+citric acid was placed in a rotoevaporator, and kept for 5 min at 90° C. and 50 mbar. 7.5 g of bleaching earth were added to the resulting material. The mixture was put again in the rotoevaporator at 90° C., 50 mbar for 30 min and then filtered in vacuum in a Buchner funnel.

After clarification, the sample was vapor distilled to remove undesirable compounds at 175° C., during a certain period of time under vacuum for 1 h.

Finally, a certain amount of a sequestering agent and a certain amount of antioxidant was added, of 2.5 g citric acid and 0.83 g BHA.

Example 2

Compositions According to the Present Invention

Example 2a

The following composition was prepared containing the *sapucainha* butter obtained according to the process described in Example 1 at the ratio of 1%, by weight:

| Component | Concentration (% w/w) |
|---|---|
| Demineralized water | 94.1500 |
| Disodium EDTA | 0.0500 |
| Carbopol ETD 2020 | 0.4500 |
| Trietanolamine | 0.4500 |
| Sapucainha butter | 1.0000 |
| Iodopropynyl butylcarbamate | 0.2000 |
| Phenoxyethanol F | 0.7000 |
| Hydroxyethyl acrylate, Acryloyldimethyl copolymer | 3.000 |

The composition above was obtained by initially preparing the aqueous phase adding EDTA to the water and waiting its total solubilization. Then, Carbopol was gradually added until its total dispersion, following by the addition of trietanolamine. For the preparation of the oily phase, the *sapucainha* butter was heated up to its melting point. After heating the aqueous phase up to the same temperature of the *sapucainha* butter, the two phases were mixed and stirred for 5 minutes. The heating ceased, the other components were added and stirring continued for additional 15 minutes.

Example 2b

The following composition was prepared containing *sapucainha* butter obtained according to the process described in Example 1 at the ratio of 3%, by weight:

| Component | Concentration (% w/w) |
|---|---|
| Demineralized water | 92.1500 |
| Disodium EDTA | 0.0500 |
| Carbopol ETD 2020 | 0.4500 |
| Trietanolamine | 0.4500 |
| Sapucainha butter | 3.0000 |
| Iodopropynyl butylcarbamate | 0.2000 |
| Phenoxyethanol F | 0.7000 |
| Hydroxyethyl acrylate, Acryloyldimethyl copolymer | 3.000 |

The composition was prepared following the same procedure described in Example 2a.

Example 2c

The following composition was prepared containing the *sapucainha* butter obtained according to the process described in Example 1 at the ratio of 5%, by weight:

| Component | Concentration (% w/w) |
|---|---|
| Demineralized water | 90.1500 |
| Disodium EDTA | 0.0500 |
| Carbopol ETD 2020 | 0.4500 |
| Trietanolamine | 0.4500 |
| Sapucainha butter | 5.0000 |
| Iodopropynyl butylcarbamate | 0.2000 |
| Phenoxyethanol F | 0.7000 |
| Hydroxyethyl acrylate, Acryloyldimethyl copolymer | 3.000 |

The composition was prepared following the same procedure described in Example 2a.

Example 2d

The following composition was prepared containing the *sapucainha* butter obtained according to the process described in Example 1 at the ratio of 10%, by weight:

| Component | Concentration (% w/w) |
|---|---|
| Demineralized water | 85.1500 |
| Disodium EDTA | 0.0500 |
| Carbopol ETD 2020 | 0.4500 |
| Trietanolamine | 0.4500 |
| Sapucainha butter | 10.0000 |
| Iodopropynyl butylcarbamate | 0.2000 |
| Phenoxyethanol F | 0.7000 |
| Hydroxyethyl acrylate, Acryloyldimethyl copolymer | 3.000 |

Comparative Examples

Comparative tests were carried out for several of the features of the present invention with regard to prior-art compositions containing silicones and fatty esters such as indicated below.

The compositions of the invention described in examples 2a to 2d above were compared with the following compositions:

Wash out formula with 5% Cyclomethicone D5 and dimethiconol (D5 5%)

| | |
|---|---|
| Demineralized water | 90.1500 |
| Disodium EDTA | 0.0500 |
| Carbopol ETD 2020 | 0.4500 |
| Trietanolamine | 0.4500 |
| Cyclomethicone D5 and dimethiconol | 5.0000 |
| Iodopropynyl butylcarbamate | 0.2000 |
| Phenoxyethanol F | 0.7000 |
| Hydroxyethyl acrylate, Acryloyldimethyl copolymer | 3.0000 |

Wash out Formula with 5% Dicaprylyl carbonate (Dicapri 5%)

| | |
|---|---|
| Demineralized water | 90.1500 |
| Disodium EDTA | 0.0500 |
| Carbopol ETD 2020 | 0.4500 |
| Trietanolamine | 0.4500 |
| Dicaprylyl carbonate | 5.0000 |
| Iodopropynyl butylcarbamate | 0.2000 |
| Phenoxyethanol F | 0.7000 |
| Hydroxyethyl acrylate, Acryloyldimethyl copolymer | 3.0000 |

Wash out formula with 5% cyclomethicone and dimethicone crosspolymer (Crossp 5%)

| | |
|---|---|
| Demineralized water | 85.1500 |
| Disodium EDTA | 0.0500 |
| Carbopol ETD 2020 | 0.4500 |
| Trietanolamine | 0.4500 |
| Cyclomethicone and dimethicone crosspolymer | 5.0000 |
| Cyclomethicone D5/D6 VS7158 | 5.0000 |
| Iodopropynyl butylcarbamate | 0.2000 |
| Phenoxyethanol F | 0.7000 |
| Hydroxyethyl acrylate, Acryloyldimethyl copolymer | 3.0000 |

Wash out formula corn 5% cetyl lactate (Lact 5%)

| | |
|---|---|
| Demineralized water | 90.1500 |
| Disodium EDTA | 0.0500 |
| Carbopol ETD 2020 | 0.4500 |
| Trietanolamine | 0.4500 |
| Cetyl lactate | 5.0000 |
| Iodopropynyl butylcarbamate | 0.2000 |
| Phenoxyethanol F | 0.7000 |
| Hydroxyethyl acrylate, Acryloyldimethyl copolymer | 3.0000 |

Wash out formula placebo (Place)

| | |
|---|---|
| Demineralized water | 95.1500 |
| Disodium EDTA | 0.0500 |
| Carbopol ETD 2020 | 0.4500 |
| Trietanolamine | 0.4500 |
| Iodopropynyl butylcarbamate | 0.2000 |
| Phenoxyethanol F | 0.7000 |
| Hydroxyethyl acrylate, Acryloyldimethyl copolymer | 3.000 |

The following characteristics were assessed:

| ATTRIBUTE | DEFINITION |
|---|---|
| Absorption point | Number of rotations needed for the product to start being absorbed by the skin |
| Spreadability | Easiness to spread the product on the skin |
| Slipperiness | Easiness to slip/slide the finger over the skin |
| Immediate Skin Gloss | Intensity of the light reflected on the skin immediately after the product is spread |
| Residual Skin Gloss | Intensity of the light reflected on the skin two minutes after the product is spread |
| Stickiness | Intensity with which the finger adheres to the skin |
| Immediate Oiliness | Oily sensation on the skin during and after the product is spread |
| Residual Oiliness | Oily sensation on the skin two minutes after the product is spread |

| ATTRIBUTE | DEFINITION |
|---|---|
| Immediate Greasy Film | Greasy sensation, forming a film on the skin, immediately after the product is spread |
| Residual Greasy Film | Greasy sensation, forming a film on the skin, two minutes after the product is spread |
| Velvety film | "Peach skin" sensation |
| White residue | Formation of the white film over the skin |

The compositions above were applied onto volunteers under the same conditions, and the results are presented in Table 2:

TABLE 2

| | Abs. Pt. | Spread | Slip. | Stick. | Im. Gloss | Res. Gloss | Velv. Film | Im. Oil. | Res. Oil. | Im. Greasy F. | Res. Greasy F. |
|---|---|---|---|---|---|---|---|---|---|---|---|
| Sapucainha Analysis 1% | | | | | | | | | | | |
| Analysis | | | | | | | | | | | |
| Sapuc 1% | 2.1 | 6.64 | 6.65 | 0.55 | 5.50 | 1.82 | 4.34 | 2.75 | 0.11 | 1.49 | 0.00 |
| D5 5% | 2.0 | 6.57 | 6.59 | 0.46 | 4.15 | 1.69 | 4.87 | 2.22 | 0.10 | 1.35 | 0.02 |
| Dicapr 5% | 1.9 | 6.46 | 6.45 | 0.54 | 4.96 | 2.34 | 4.42 | 3.28 | 0.27 | 1.61 | 0.03 |
| Cressp 5% | 2.0 | 6.61 | 6.70 | 0.28 | 4.53 | 1.22 | 4.65 | 2.50 | 0.05 | 1.34 | 0.00 |
| Lact 5% | 1.8 | 6.31 | 6.35 | 0.43 | 3.83 | 1.91 | 4.66 | 2.04 | 0.19 | 1.25 | 0.04 |
| Place | 2.1 | 6.67 | 6.72 | 0.67 | 5.42 | 1.60 | 4.77 | 2.28 | 0.06 | 1.44 | 0.02 |
| Sapucainha Analysis 3% | | | | | | | | | | | |
| Products | | | | | | | | | | | |
| Sapuc 3% | 2.0 | 6.35 | 6.33 | 0.54 | 4.87 | 2.84 | 4.59 | 2.65 | 0.17 | 1.80 | 0.08 |
| D5 5% | 1.9 | 6.57 | 6.59 | 0.46 | 4.15 | 1.69 | 4.87 | 2.22 | 0.10 | 1.35 | 0.02 |
| Dicapr 5% | 1.6 | 6.46 | 6.45 | 0.54 | 4.96 | 2.34 | 4.42 | 3.28 | 0.27 | 1.61 | 0.03 |
| Cressp 5% | 2.0 | 6.61 | 6.70 | 0.28 | 4.53 | 1.22 | 4.65 | 2.50 | 0.05 | 1.34 | 0.00 |
| Lact 5% | 1.8 | 6.31 | 6.35 | 0.43 | 3.83 | 1.91 | 4.66 | 2.04 | 0.19 | 1.25 | 0.04 |
| Place | 2.1 | 6.67 | 6.72 | 0.67 | 5.42 | 1.60 | 4.77 | 2.28 | 0.06 | 1.44 | 0.02 |
| Sapucainha Analysis 5% | | | | | | | | | | | |
| Products | | | | | | | | | | | |
| Sapuc 5% | 2.0 | 6.29 | 6.20 | 1.02 | 5.03 | 2.98 | 4.59 | 2.92 | 0.34 | 1.48 | 0.1908 |
| D5 5% | 1.9 | 6.57 | 6.59 | 0.46 | 4.15 | 1.69 | 4.87 | 2.22 | 0.10 | 1.35 | 0.02 |
| Dicapr 5% | 1.6 | 6.46 | 6.45 | 0.54 | 4.96 | 2.34 | 4.42 | 3.28 | 0.27 | 1.61 | 0.03 |
| Cresp 5% | 2.0 | 6.61 | 6.70 | 0.28 | 4.53 | 1.22 | 4.65 | 2.50 | 0.05 | 1.34 | 0.00 |
| Lact 5% | 1.8 | 6.31 | 6.35 | 0.43 | 3.83 | 1.91 | 4.66 | 2.04 | 0.19 | 1.25 | 0.04 |
| Place | 2.1 | 6.67 | 6.72 | 0.67 | 5.42 | 1.60 | 4.77 | 2.28 | 0.06 | 1.44 | 0.02 |
| Sapucainha Analysis 10% | | | | | | | | | | | |
| Products | | | | | | | | | | | |
| Sapuc 10% | 2.0 | 6.43 | 6.36 | 0.77 | 5.18 | 3.35 | 4.80 | 3.52 | 0.92 | 1.92 | 0.54 |
| D5 5% | 2.0 | 6.57 | 6.59 | 0.46 | 4.15 | 1.69 | 4.87 | 2.22 | 0.10 | 1.35 | 0.02 |
| Dicapr 5% | 1.9 | 6.46 | 6.45 | 0.54 | 4.96 | 2.34 | 4.42 | 3.28 | 0.27 | 1.61 | 0.03 |
| Cresp 5% | 2.0 | 6.61 | 6.70 | 0.28 | 4.53 | 1.22 | 4.65 | 2.50 | 0.05 | 1.34 | 0.00 |
| Lact 5% | 1.8 | 6.31 | 6.35 | 0.43 | 3.83 | 1.91 | 4.66 | 2.04 | 0.19 | 1.25 | 0.04 |
| Place | 2.1 | 6.67 | 6.72 | 0.67 | 5.42 | 1.60 | 4.77 | 2.28 | 0.06 | 1.44 | 0.02 |

The results show that the compositions of the present invention using the *sapucainha* butter instead of silicones and fatty esters do not lose the desired features for a topical composition. It was possible to confirm that the *sapucainha* butter has attributes such as absorption point, spreadability, slipperiness, residual oiliness and immediate oiliness which are similar to those of fatty esters, such as cetyl lactate and dicaprylyl carbonate, and silicones, such as cyclomethicone and dimethicone crosspolymer and cyclomethicone D5 and dimethiconol, when applied at a certain concentration in emulsion.

The invention claimed is:

1. A process for preparing a *sapucainha* oil or butter product comprising the steps of:
   a) providing seeds from a *sapucainha* plant;
   b) drying and pressing said seeds to obtain an oil;
   c) filtering the oil obtained in step (b) to obtain a filtrate;
   d) contacting the filtrate obtained in step (c) with an organic acid and an acid-activated clay to obtain a treated material;
   e) maintaining the treated material obtained in step (d) under vacuum for a suitable period of time until the treated material becomes clear to obtain a clarified material;
   f) filtering the clarified material obtained in step (e) and submitting the resulting filtrate to vapor distillation to obtain a distillate; and
   g) adding a sequestering agent and an antioxidant agent to the distillate to obtain said *sapucainha* oil or butter product,
   wherein the sequestering agent is selected from the group consisting of citric acid, phosphoric acid, and oxalic acid; and the antioxidant is selected from the group consisting of butylhydroxyanisole, ter-butyl hydroquinone, and butylated hydroxytoluene.

2. The process according to claim 1, wherein the *sapucainha* plant is selected from the group consisting of *Hyaraktogenos kurzii, Hydnocarpus wightiana, Hydnocarpus heterophylla, Hydnocarpus anthelmintica, Hydnocarpus alpina, Hydnocarpus cauliflora, Hydnocarpus dawnensis, Hydnocarpus hutchinsonni, Hydnocarpus ovoidea, Hydnocarpus subfalcata, Hydnocarpus venenata, Hydnocarpus verrucosa, Hydnocarpus woodii, Oconba echinata, Caloncoba welwitschii, Carpotroche bahiensis, Carpotroche brasiliensis, Carpotroche brasiliensis* var. *bahiensis, Carpotroche brasiliensis* var. *longifolia, Asteriastigma macrocarpa, Mayna brasiliensis, Mayna odorata, Lindakeria dentata* and *Caloncoba glauca*.

3. The process according to claim 2, wherein the *sapucainha* plant is *Carpotroche brasiliensis*.

4. The process according to claim 1, wherein at step (c) a filtering agent is used, and is selected from the group consisting of silicon oxide, aluminum oxide, ferric oxide, calcium oxide, magnesium oxide, sodium oxide, and potassium oxide.

5. The process according to claim 1, wherein the organic acid used in step (d) is selected from the group consisting of citric acid, phosphoric acid, and oxalic acid.

6. The process according to claim 1, wherein in step (e), the treated material is maintained under vacuum for 15-60 min at a temperature ranging from 0 to 100° C.

7. The process according to claim 1, wherein the distillation step (f) is carried out at a temperature ranging between 160° and 240° C. for 1 to 2 hours.

8. The process according to claim 1, wherein in step (g) the sequestering agent is added in an amount of 0.1 to 1% by weight and the amount of the antioxidant is added in an amount of 0.01 to 0.1%, by weight, based on the weight of the distillate.

9. The process according to claim 1, further comprising incorporating said *sapucainha* oil or butter product into a silicon-free cosmetic or pharmaceutical composition.

* * * * *

UNITED STATES PATENT AND TRADEMARK OFFICE
CERTIFICATE OF CORRECTION

PATENT NO. : 9,492,372 B2  Page 1 of 1
APPLICATION NO. : 12/666397
DATED : November 15, 2016
INVENTOR(S) : Fernandes de Oliveira et al.

It is certified that error appears in the above-identified patent and that said Letters Patent is hereby corrected as shown below:

In the Claims

Column 12,
Line 1, "*Hydnocarpus anthelmintica*" should read --*Hydnocarpus antheimintica*--.

Signed and Sealed this
Eleventh Day of July, 2017

Joseph Matal
*Performing the Functions and Duties of the
Under Secretary of Commerce for Intellectual Property and
Director of the United States Patent and Trademark Office*